United States Patent [19]
Hill et al.

[11] Patent Number: 5,195,948
[45] Date of Patent: Mar. 23, 1993

[54] ADJUSTABLE BACK SUPPORT DEVICE

[76] Inventors: Dennis M. Hill, 23931 SE. 25th Ct., Issaquah, Wash. 98027; Richard T. Wenala, 16606 162 NE., Woodinville, Wash. 98072

[21] Appl. No.: 847,663

[22] Filed: Mar. 5, 1992

[51] Int. Cl.[5] ............................................. A61F 5/00
[52] U.S. Cl. .................................................... 602/19
[58] Field of Search .................... 128/876, DIG. 20; 602/5, 12, 13, 19, 23, 36

[56] References Cited

U.S. PATENT DOCUMENTS

| | | | |
|---|---|---|---|
| 1,646,500 | 4/1926 | Mildenberg. | |
| 3,441,027 | 4/1969 | Lehman | 602/19 |
| 3,521,623 | 7/1970 | Nichols | 602/13 |
| 4,135,503 | 1/1979 | Romano | 602/13 |
| 4,178,923 | 12/1979 | Curlee | 602/13 |
| 4,597,386 | 7/1986 | Goldstein | 602/19 |
| 4,622,957 | 11/1986 | Curlee | 602/19 |
| 4,682,587 | 7/1987 | Curlee | 602/13 |
| 4,682,588 | 7/1987 | Curlee | 602/13 |
| 4,756,306 | 7/1988 | Curlee | 602/19 |
| 4,794,916 | 1/1989 | Porterfield | 602/19 |
| 4,991,572 | 2/1991 | Chases | 602/13 |
| 4,993,409 | 2/1991 | Grim | 602/19 |
| 5,062,414 | 11/1991 | Grim | 602/19 |

*Primary Examiner*—Robert A. Hafer
*Assistant Examiner*—Michael Brown
*Attorney, Agent, or Firm*—Dean A. Craine

[57] ABSTRACT

A back support device is disclosed comprising a belt structure designed to fit substantially around the waist of a user. An inflatable air bladder is attached inside the belt structure so that it is positioned adjacent to the lower back when the back support device is worn. Several embodiments of elastic strap members are disclosed which are attached between the air bladder and belt structure. The strap members enable the user to adjust the direction of force exerted by the air bladder on the lower back and helps to pull the air bladder around the waist. A manual air plump with two-way valve is positioned inside the belt structure near one end which enables the user to selectively adjust the amount of air in the air bladder while the back support device is worn. Using the above device, a method of providing back support is also disclosed.

11 Claims, 6 Drawing Sheets

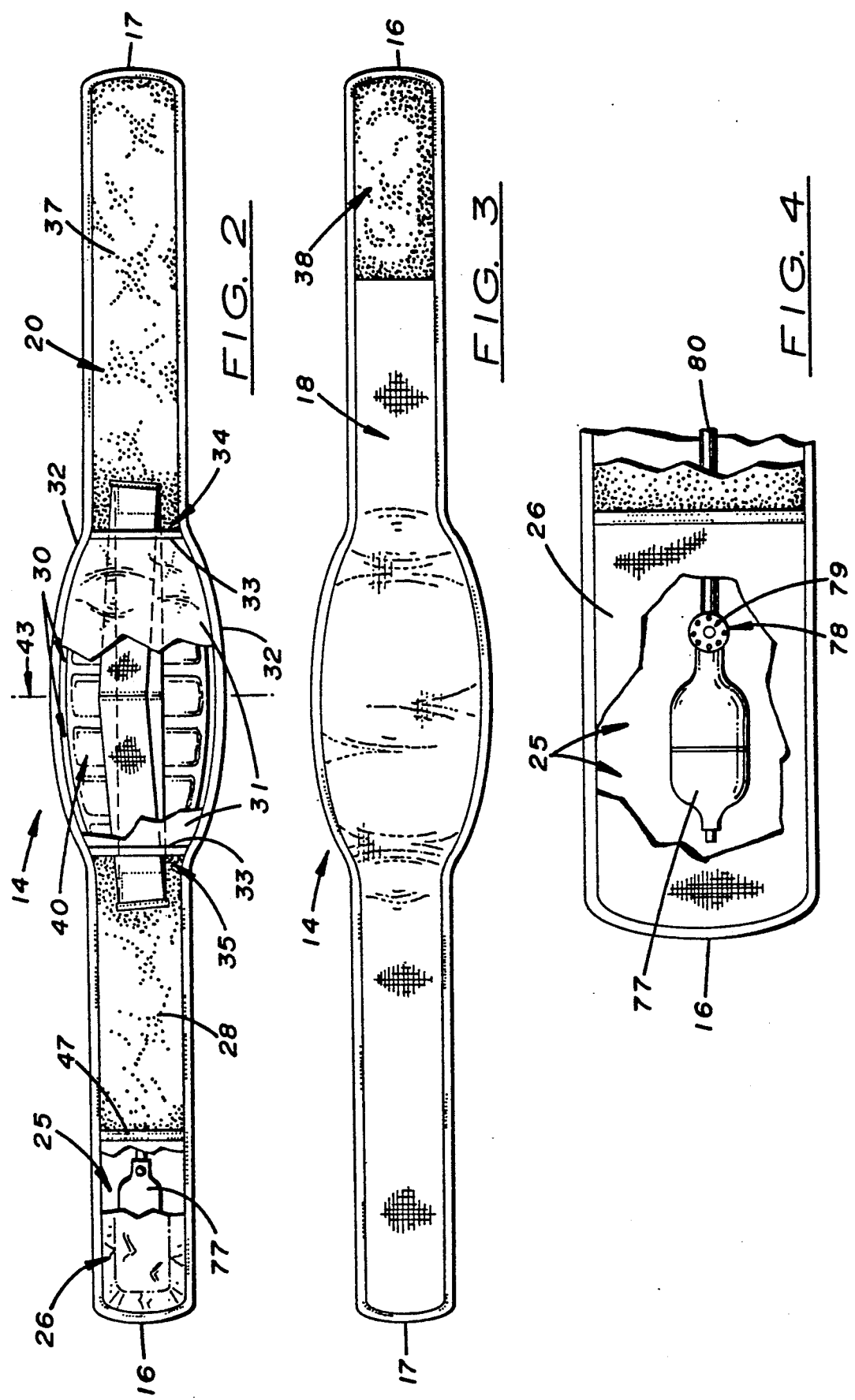

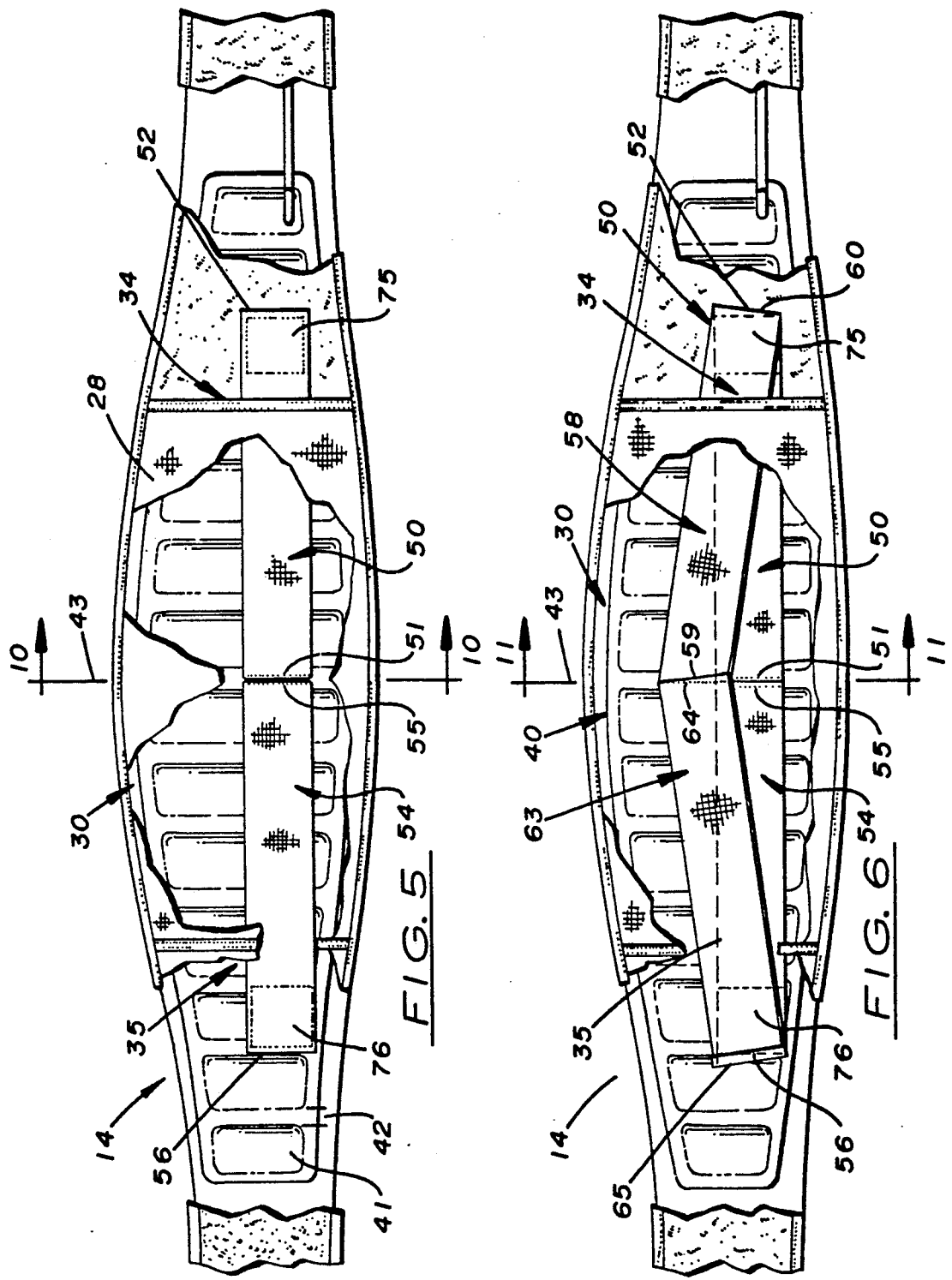

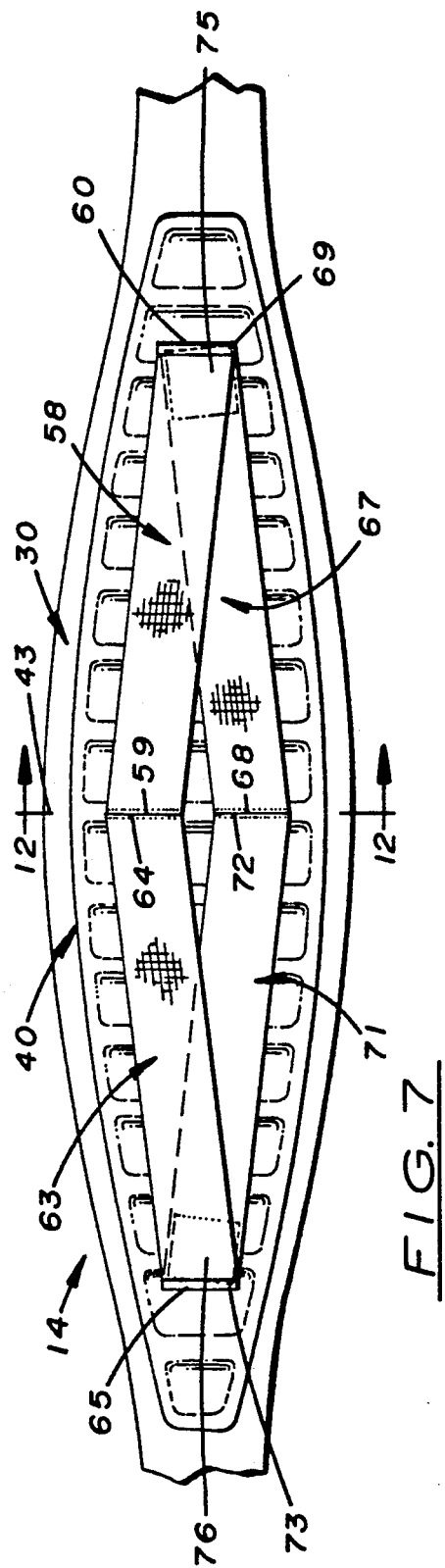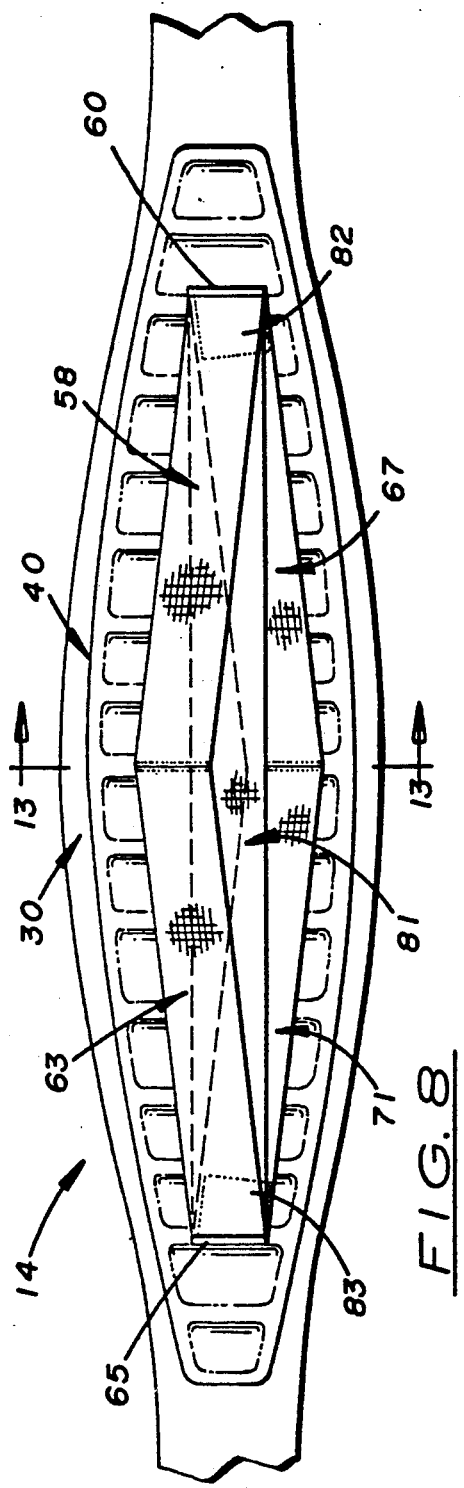

ADJUSTABLE BACK SUPPORT DEVICE

BACKGROUND OF THE INVENTION

1. Field of the Invention

This invention relates generally to back support devices, and more particularly to inflatable, belt-shaped back support devices.

2. Description of the Related Art

It is widely known that back injuries are very debilitating and one of the leading causes of absenteeism in the work place. In the U.S. alone each year, millions of dollars are spent on medical treatment of back injuries and lost due to reduced productivity in the work place.

Back pain is caused by injuries which result in misaligned vertebra, bulging or ruptured discs located between vertebra, or back muscle spasms. Today, rest, support, and immobilization of the back are often prescribed for treatment of back injuries. Unfortunately, such rest and immobilization in combination with the pain, often causes depression and lost productivity.

Many devices and techniques have been used to treat back injuries. One device, known as a back support devices have been used primarily to support and to immobilize the injured back area. Many back support devices use an inflatable bladder that presses against the lower back area when the back support device is worn.

Over the last sixty years, several improvements have been made in back support devices and air bladder technology. One of the original back support devices having an inflatable bladder was disclosed by Mildenbero in U.S. Pat. No. 1,646,590. In U.S. Pat. No. 4,178,923, Curlee shows an improved back support device comprising a corset made of one-piece, synthetic plastic material, with an air bladder attached thereto. In U.S. Pat. No. 4,622,957, Curlee offers an improved therapeutic corset designed to apply more precisely counter-pressures to the lower back. This improved therapeutic corset comprises a rigid yet bendable belt support surface and an inflatable air bladder which is divided into intercommunicating cells. When inflated, the air bladder assumes a desirable bend which conforms to the user's body.

In U.S. Pat. No. 4,682,587, Curlee discloses another improved back support device called a compound force sacrolumbar support belt which, when worn, supports the wearer's back and pulls the abdominal wall toward the spine. The two-way force effect, is reportedly brought about by: (1) the inflation of the specially designed bladder forming a rigid yet flexible support structure across the back and; (2) a simultaneous tightening of the belt or corset material by strapping or buckling in a conventional manner the front or side. When the bladder is inflated during use, it presses into the back. At the same time, belt is drawn tighter which further presses the bladder into the back and pulls the abdominal wall towards the spine. In order to create the compound force, a flat envelope is securely attached to the support belt or corset. The envelope is sectioned into a series of vertical ribs formed perpendicular to the longitudinal axis of the support belt or corset. The length of the entire envelope is longer than its height which cause the envelope to shrink in size along its longitudinal axis when inflated. Because the envelope is securely attached the belt or corset, when the envelope is inflated the belt or corset is drawn tighter and pulls the bladder into the spine and the abdomen inward toward the spine.

In U.S. Pat. No. 4,993,409, Grim discloses another improved inflatable back support device comprising a back brace made of elastic material which carries a removable pad filled with a gel-like substance. The back brace also includes an air bladder which presses the pad into the spine of the user during use. The air bladder includes a plurality of chambers which are individually inflated by the user. Releasable straps are attached to the edges of the air bladder and are used to attach the air bladder to the back brace and to adjust of the pressure exerted by the bladder on the lower back.

There are several drawbacks with the back support devices discussed above. First, such devices can not be easily adjusted to provide optimal back support to different areas of the lower back. Second, such devices can not be adjusted while worn by the user to provide optimal support and comfort. A third drawback is that such devices can not be adjusted for movement. A fourth drawback is that such devices are not self-contained and therefore, not well suited for use in the work place.

A back support device which addresses and overcome these and other drawbacks discussed further herein, would be highly desirable.

SUMMARY OF THE INVENTION

It is a general object of the present invention is to provide an improved back support device which provides optimal back support.

It is another object of the present invention to provide a back support device which may be adjusted for greater comfort and optimal support while the device is worn.

It is a further object of the present invention to provide a back support device that is a self-contained unit which enables the device to be worn in different environments, such as in the home or work place.

It is another object of the present invention to provide a back support device which may worn by users to prevent possible back injuries.

It is still another object of the present invention to provide a back support device which is relatively inexpensive and easy to manufacture.

The back support device disclosed herein comprises a belt structure, an air bladder, an air inflation means, and an adjustable air bladder positioning means. The belt structure is designed to fit substantially around the user's waist.

The air bladder is positioned inside the belt structure so that when the belt structure is worn around the waist, the air bladder is positioned adjacent to the user's lower back. In the preferred embodiment, the air bladder comprises a plurality of vertically aligned, inflatable ribs. The ribs are manufactured in the air bladder so that air bladder may be easily bent around user's waist or lower back when inflated.

The inside surface of the belt structure is made of durable, lightweight material elastic material which limits stretching on the belt structure along its longitudinal axis. A continuous selvage member is sewn along the peripheral edge of the belt structure to attach the materials used to cover the inside and outside surfaces together, and to prevent stretching of the belt structure along its longitudinal axis. This "non-stretchable" feature, allows the belt structure to function like a corset thereby providing support to the lower back when worn. In addition, the "non-stretchable" feature enables the adjustable air bladder position means, discussed below, to reduce the overall length of the belt structure thereby providing another method for adjusting the amount of support provided over the user's lower back. The outside surface of the belt structure is made of durable, loop fabric material.

An adjustable belt holding means is attached to the belt structure which adjustably holds the belt structure around the user's waist. In the preferred embodiment, the adjustable belt holding means comprises a pad of hook fabric material which is attached to the inside surface of the belt structure near the first end. During use, the pad engages the loop fabric material located on the outside surface near the second end of the belt structure to hold the belt structure around the user's waist. It should be understood, however, that other types of adjustable belt holding means, such as snaps or buckles, which perform the same function as the pad of hook fabric material and outside surface of loop fabric material, could be used in place thereof.

The air inflation means is conveniently disposed inside the front section of the belt structure. It is connected to the air bladder and allows the user to selectively adjust the amount of air in the air bladder while the belt structure is worn. By disposing the air inflation means inside the front section of the belt structure in this manner, no external objects are attached to or hang from the outside surface of the belt structure. It addition, the back support device acts as a single, self-containing unit which allows the user to immediately and easily adjusted the back support device while it is worn. This feature also allows the back support device to be used continuously in a wide variety of different environments or activities, such as the home or work place.

The adjustable air bladder positioning means is used to adjust the direction and amount of force exerted by the air bladder on the lower back when the device is worn. Four different air bladder positioning means, which all adjust the air bladder in a unique manner, are disclosed herein. In one embodiment, the air bladder positioning means comprise two elastic, horizontal strap members each attached at a first end to the air bladder along its vertical midline axis. The horizontal strap members extend laterally across the outside surface of the air bladder in opposite directions. The second end of each horizontal strap member extends through the vertically aligned opening located on the sides of the bladder cavity. When the horizontal strap members are pulled middle section of the air bladder is forced laterally, the middle section of the air bladder is forced inwardly. At the same time, the air bladder is curved or bent around the user's waist. By adjusting the length of the horizontal strap members, the user can adjust the amount and direction of force exerted by the air bladder on the lower back.

In a second embodiment, the adjustable air bladder positioning means comprises two elastic horizontal strap members used in the first embodiment and two elastic, downward diagonal strap members. Each downward diagonal strap member is attached at a first end to the air bladder along its vertical midline axis above the attachment point of the first ends of the horizontal strap members. The second ends of the downward diagonal strap members extend downward and laterally across the air bladder in opposite direction and attached to the second end of the adjoining horizontal strap member. The second ends of the diagonal downward and the horizontal strap members are sewn together to form one extending end that projects from the opening in the bladder cavity. When the two extending ends are pulled laterally, the air bladder is curved around the waist and the middle and upper sections of the air bladder are forced into the lower back.

In a third embodiment, the adjustable air bladder comprises two elastic, downward diagonal strap members as described above in the second embodiment and two elastic, upward diagonal strap members. The first end of each upward diagonal strap member is attached to the air bladder along the vertical midline axis slightly below the air bladder's horizontal midline axis. The second ends of the upward diagonal strap member and the adjoining downward diagonal strap member located on each side of the air bladder are sewn together to form one extending end that extends through the adjacent opening into the bladder cavity. When the extending ends are pulled laterally, the upper and lower sections of the air bladder are curved around the waist and forced into the lower back.

In a fourth embodiment, the adjustable air bladder positioning means comprises the same straps members used in the third embodiment. In addition, however, an elastic, free floating horizontal strap member is attached between the two opposite extending ends. When the extending ends are pulled laterally, the upper, middle, and lower sections of the air bladder are curved around the waist and forced into the lower back.

To hold the extending ends of the straps in their selected positions, a hook fabric pad is attached to the inside surface of the inner most strap member near the extending end. During use, the user presses the hook fabric pad into the loop fabric material located on the outside surface of the belt structure. As discussed above, when the extending ends are pulled, the air bladder is curved around and sections of the air bladder are forced into the user's lower back. When the strap members engage the outside surface of the belt structure, the sides of the belt structure on opposite sides of the bladder cavity are pulled together with reduces the overall circumference of the belt structure. This, in turn, further forces the air bladder into the user's lower back.

Using the back support device disclosed herein, a novel method for supporting the lower back is provided. After the device is initially attached to the waist, the user may adjust the back support device by any of the following single or combined acts: (1) adjusting the location of the extending ends of the strap members on the outside surface of the belt structure; (2) adjusting the length of the belt structure, and; (3) adjusting the amount of air in the air bladder.

BRIEF DESCRIPTION OF THE DRAWINGS

FIG. 2 is a front elevational view partially cut away showing the outside surface of the back support device.

FIG. 3 is a rear elevational view of the inside surface of the back support device.

FIG. 4 is a sectional, elevational view of the back support device showing the hand pump disposed in the tongue cavity near the first end of the belt structure.

FIG. 5 is a rear, sectional, elevational view of the back support device showing the air bladder and the first embodiment of the adjustable air bladder positioning means attached thereto.

FIG. 6 is a rear, sectional, elevational view of the back support device similar to FIG. 5 showing the air bladder and a second embodiment of the adjustable air bladder positioning means attached thereto.

FIG. 7 is a rear, sectional, elevational view of the back support device similar to FIGS. 5 and 6 showing the air bladder and a third embodiment of the adjustable air bladder positioning means attached thereto.

FIG. 8 is a rear, sectional, elevational view of the back support device similar to FIGS. 5, 6 and 7 showing the air bladder and a fourth embodiment of the adjustable air bladder positioning means attached thereto.

DESCRIPTION OF THE PREFERRED EMBODIMENTS

Referring specifically to the accompanying FIGS. 1–8 wherein like numerals refer to like parts, there is shown an adjustable, back support device 10. The back support device 10 comprises a belt structure 14 designed to fit comfortably around the waist of a user. Disposed inside the belt structure 14 is an inflatable air bladder 40 which during use is pressed into the user's lower back to provide support.

Figure 1:
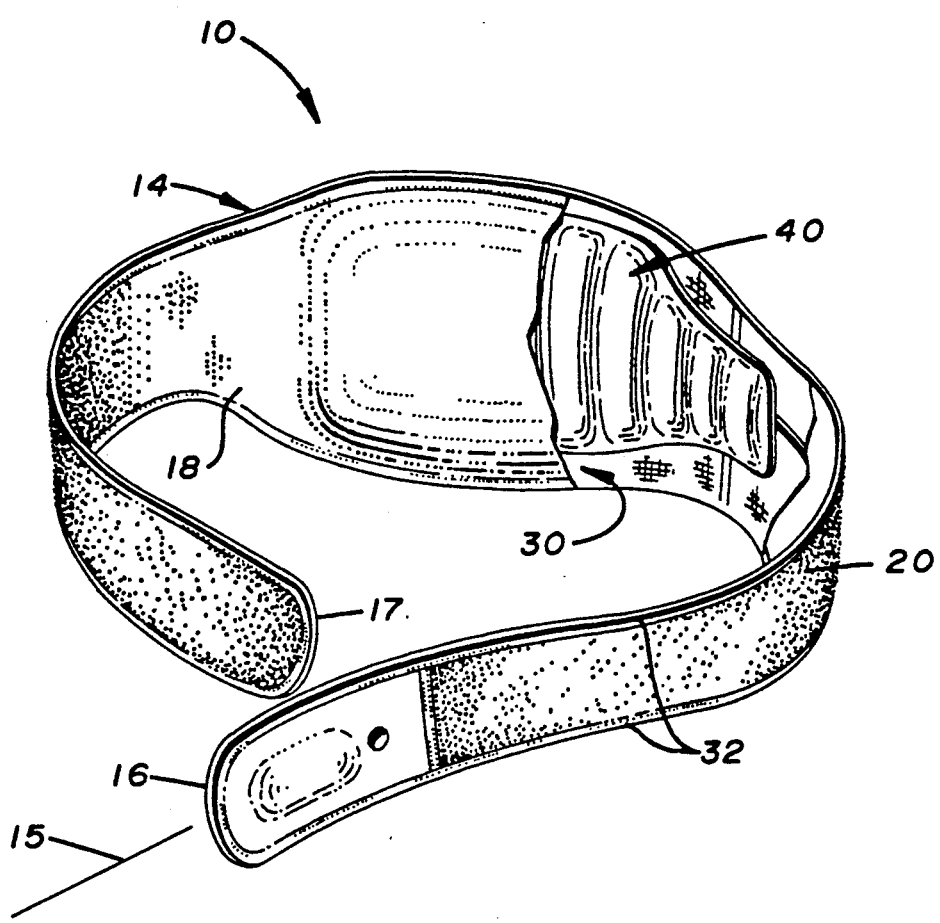
FIG. 1 is a perspective view partially cut away showing of the back support device.

As shown in FIG. 1, belt structure 14 has a first end 16, a second end 17, an inside surface 18, and an outside surface 20. The inside surface 18 and outside surface 20 are made of thin, flexible materials which resists stretching along the belt structure's longitudinal axis. In the preferred embodiment, inside surface 18 is made of elastic, synthetic material with limited expansion or stretching qualities in one direction. During manufacture of the belt structure 14, the inside surface 18 material is aligned on the belt structure 14 so that it has limited expansion or stretching qualities in the direction parallel to the belt structure's longitudinal axis 15. Such material may be expanded or stretched in the direction perpendicular to the belt structure's longitudinal axis which allows the belt structure 14 to easy conform to the user's outer clothing or figure. In the preferred embodiment, the inside surface 18 is made of synthetic elastic material known generically as "SPANDEX" or "LYCRA SPANDEX", sold by such companies as E.I. Du Pont De Nemours and Company, Delaware, U.S.A.

A continuous selvage member 32 made of nylon or some other non-stretchable material is sewn around the peripheral edge of the belt structure 14. In addition to attaching the inside and outside surfaces 18 and 20 together, as described below, selvage member 32 also prevents stretching of the belt structure 14 along its longitudinal axis 15.

In the preferred embodiment, outside surface 20 comprises four sections of material sewn to the inside surface 18 along their edges along with selvage member 32. As shown in FIG. 2, the front or first section 26 near first end 16 covers a tongue cavity 25 in which a hand pump 77 is disposed. The material used in first section 26 is durable and washable, such as nylon pack cloth. The first section 26 is also sufficiently thin so that the user may manually squeeze the hand pump 77 located in the tongue cavity 25 during use.

The second section 28 of the outside surface 20 extends from the first section 26 to the left lateral edge of the third section 31. The second section 28 is made of fabric loop material. Selvage member 47 is sewn vertically between the first and second sections 26 and 28, respectively, to join the two sections together.

The third section 31, which is made of durable material similar to the material used in the first section 26, covers the outside surface of the bladder cavity 30 located centrally in the belt structure 14. The upper and lower edges of the third section 31 are sewn to selvage member 32 while the right and left lateral edges of the third section 31 are sewn to vertically aligned selvage members 33. The top and bottom edges of each selvage member 33 are sewn to the selvage member 32 to further secure the third section 31 to the belt structure 14. The central portion of each selvage member 33 is unattached thereby creating a right and a left vertically aligned opening 34 and 35, respectively, into the bladder cavity 30. The size of the openings 34 and 35 are sufficient so that the extended ends of the straps which make up the adjustable air bladder position means discussed further below, may be extended through.

The fourth section 37 of the outside surface 20 extends from the right lateral edge of the third section 31 to the second end 17 of belt structure 14. In the preferred embodiment, the fourth section 37 is covered with fabric loop material similar to the material used to cover second section 28.

As shown in FIG. 3, a rectangularly-shaped pad 38 made of fabric hook material is sewn or glued tc the inside surface 18 of the belt structure 14 near the first end 16. Pad 38 acts as an adjustable belt holding means which adjustable holds the belt structure 14 in place around the waist. During use, the user wraps the belt structure 14 around his or her waist and then presses pad 38 into the fabric loop material located on the fourth section 37.

Unlike conventional inflatable back supports, back support device 10 has an air inflation means disposed inside the belt structure 14. As shown in FIG. 4, the air inflation means comprises a hand pump 77 and an air tube 80. The hand pump 77 is disposed inside the tongue cavity 25 located on the belt structure 14 across the user's abdominal region when the belt structure 14 is worn. The hand pump 77 enables the user to manually inflate the air bladder 40 while the back support device 10 is worn. A two-way valve 78 is attached to the hand pump 77 which allows the user to manually control the inlet and outlet of air from the air bladder 40. The handle 79 of the two-way valve 78 extends through the outer surface of the first section 26 to allow easy control.

As shown in FIGS. 2 and 5–8, the inflatable air bladder 40 is disposed inside the bladder cavity 30. The air bladder 40 is sufficiently large to substantially cover the user's lower back when back support device 10 is worn. As shown in FIG. 5, air bladder 40 comprises a plurality of vertically aligned ribs 41 which, when inflated, exert pressure on the user's lower back. Non-inflating spaces 42 are manufactured between each rib 41 which enables the air bladder 40 to be forcibly bent or curved around the user's waist during use.

An adjustable air bladder positioning means is attached to the air bladder 40 which allows the user to selectively adjust the amount and direction of the forces exerted by the air bladder 40 on the user's lower back. As shown in FIGS. 5-8, there are four different pull straps embodiments disclosed herein. In the first embodiment, shown in FIG. 5, the air bladder positioning means comprises two horizontal elastic strap members 50 and 54 attached at a first end 51 and 55, respectively, to the air bladder 40 along its vertical midline axis 43. The strap members 50 and 54 are extended laterally across the outside surface of the air bladder 40 so that the second ends 52 and 56 of straps members 50 and 54, respectively, project laterally through openings 34 and 35. Hook fabric pads 75 and 76 are attached to the inside surface near second ends 52 and 56, respectively.

Figure 10:
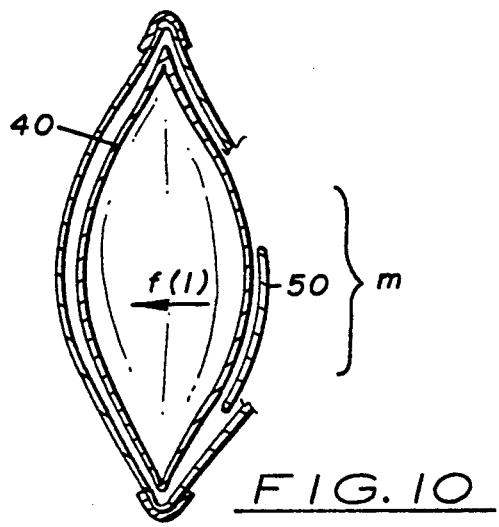
FIG. 10 is a sectional, elevational view along line 10—10 taken in FIG. 5.

As shown in FIG. 10, when the horizontal straps (50 shown) are pulled, an inward, horizontal force f(1) is exerted on the outside surface of the air bladder 40. This causes the air bladder 40 to exert pressure horizontally into the user's back for greater support.

A second embodiment of the air bladder positioning means is shown in FIG. 6, comprises the two horizontal strap members 50 and 54 described above, and two downward diagonal elastic strap members 58 and 63. The downward diagonal strap members 58 and 63 are attached at a first end 59 and 64, respectively to the outside surface of the air bladder 40 along vertical midline axis 43. The opposite second ends 60 and 65 of the downward diagonal strap members 58 and 63 are sewn or glued over the outside surface of the horizontal strap members 50 and 54, near second ends 52 and 56, respectively. During assembly, the horizontal strap members 50 and 54 are extended across the outer surface of the air bladder 40 through openings 34 and 35 of the bladder cavity 30.

Figure 11:
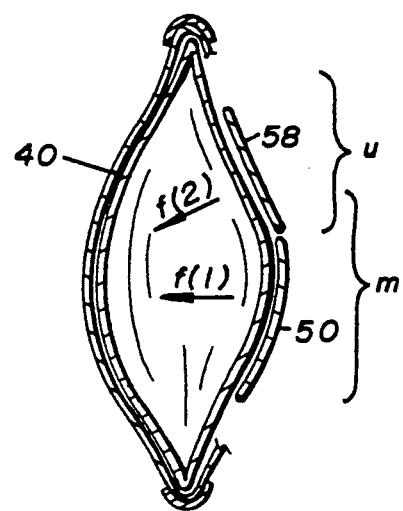
FIG. 11 is a sectional, elevational view along line 11—11 taken in FIG. 6.

As shown in FIG. 11, during use, when the second ends 52 and 56 are pulled, an inward horizontal force f(1) is exerted by the horizontal strap members (horizontal strap member 50 shown) on the middle section, denoted "m", of the air bladder 40 to force air bladder 40 into the user's lower back. At the same time, the downward diagonal strap members (strap member 58 shown), exerts a downward force f(2) on the air bladder 40 forcing the upper section, denoted "u", of the air bladder 40 into the user's lower back.

In a third embodiment, shown in FIG. 7, the air bladder positioning means comprises two upward diagonal strap members 67 and 71 and two downward diagonal elastic strap 58 and 63. Each diagonal strap 58, 63, 67 and 71 are attached at their first ends 59, 64, 68 and 72, respectively, to the outside surface of the air bladder 40 along vertical midline 43. The second ends 69 and 73 of strap members 67 and 71 are sewn or attached to the second ends 60 and 65 of the downward diagonal strap members 58 and 63, respectively.

Figure 12:
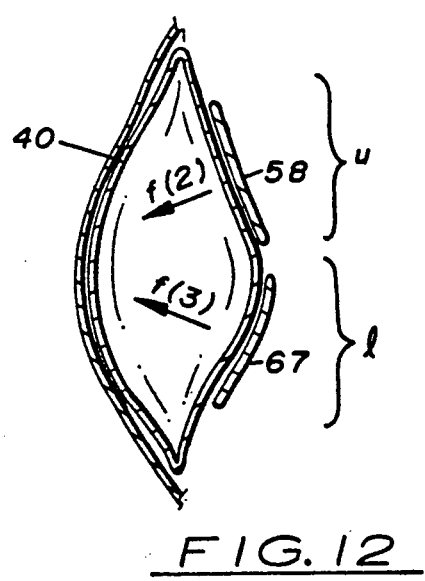
FIG. 12 is a sectional, elevational view along line 12—12 taken in FIG. 7.

As shown in FIG. 12, during use, when the downward diagonal straps members (strap member 58 shown) are pulled laterally, an inward force f(2) is exerted on the upper section "u" of the air bladder 40 to force air bladder 40 diagonally downward into the user's lower back. At the same time, the upward diagonal strap members (strap member 71 shown), exert an upward force f(3) on the lower section "l" of the air bladder 40 forcing the lower section "l" diagonally upward into the user's lower back.

In a fourth embodiment, the air bladder positioning means, shown in FIG. 8, comprises two upward diagonal straps members, 67 and 71, and two downward diagonal strap members 58 and 63. Strap members 58, 63, and 67 and 71 function in the same manner as described above in the third embodiment of he air bladder positioning means. In addition, however, an elastic, free-floating horizontal strap member 81 is wrapped around the outside surface of the air bladder 40 and attached at ends 82 and 83 to the second ends 60 and 65 of strap members 58 and 63.

Figure 13:
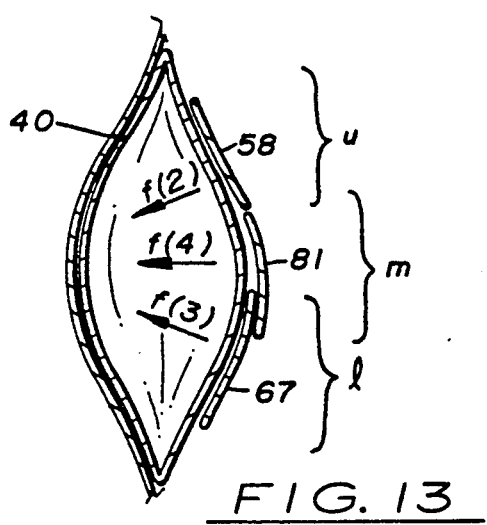
FIG. 13 is a sectional, elevational view along line 13—13 taken in FIG. 8.

As shown in FIG. 13, during use, when strap members 58, 63, 67, and 71 are pulled, forces f(2) and f(3) are exerted on the air bladder 40 in the same manner as described above. Free floating horizontal strap member 81 exerts a horizontal force f(4) across the horizontal midline of the air bladder 40 forcing the middle section "m" of the air bladder 40 into the user's lower back. Free floating horizontal strap member 81 is used in place of horizontal strap members 50 and 54 when it is desirable to prevent the middle section "m" of the air bladder 40 from protruding outward which may occur, for example, when the strap members 58, 63, 67 and 71 are pulled too tight.

Figure 9:
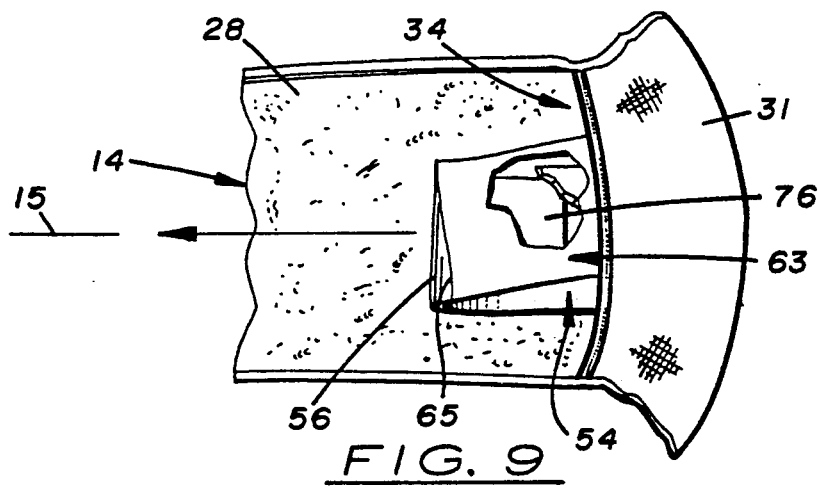
FIG. 9 is a sectional, elevational view of a extending end extending from the bladder cavity.

A shown in FIG. 9, the second ends 56 and 65 of the strap members 54 and 63 extend through the openings (opening 35 shown) into the bladder cavity. The ends 56 and 65 are sewn together and pulled over the outside surface of the second and third sections (section 28 shown) of the belt structure 14 in a direction parallel to the belt structure's longitudinal axis 15. When the desired amount of force is exerted by the air bladder 40 on the lower back, the hook engaging pads (76 shown) sewn or glued to the inside surface of the strap members are pressed into the loop fabric surface to hold them in place. The hook fabric pads 75 and 76 enable the user to selectively adjust the position of the strap members so that the desired amount of pressure is exerted by the air bladder 40 into the lower back.

Figure 14A:
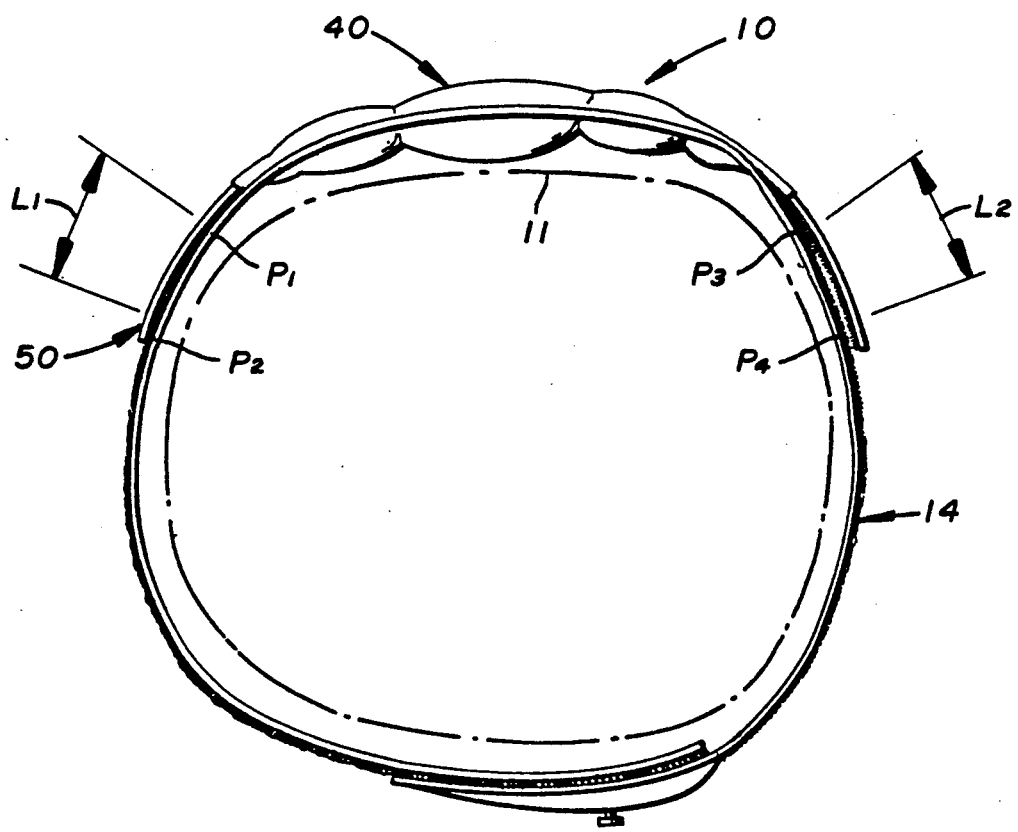
FIGS. 14(a) and 14(b) are plan views of the back support device worn by a user showing how the length of the belt structure may be educed and how the air bladder is forcibly around the waist of the user when the adjustable air bladder positioning means are pulled.
Figure 14B:
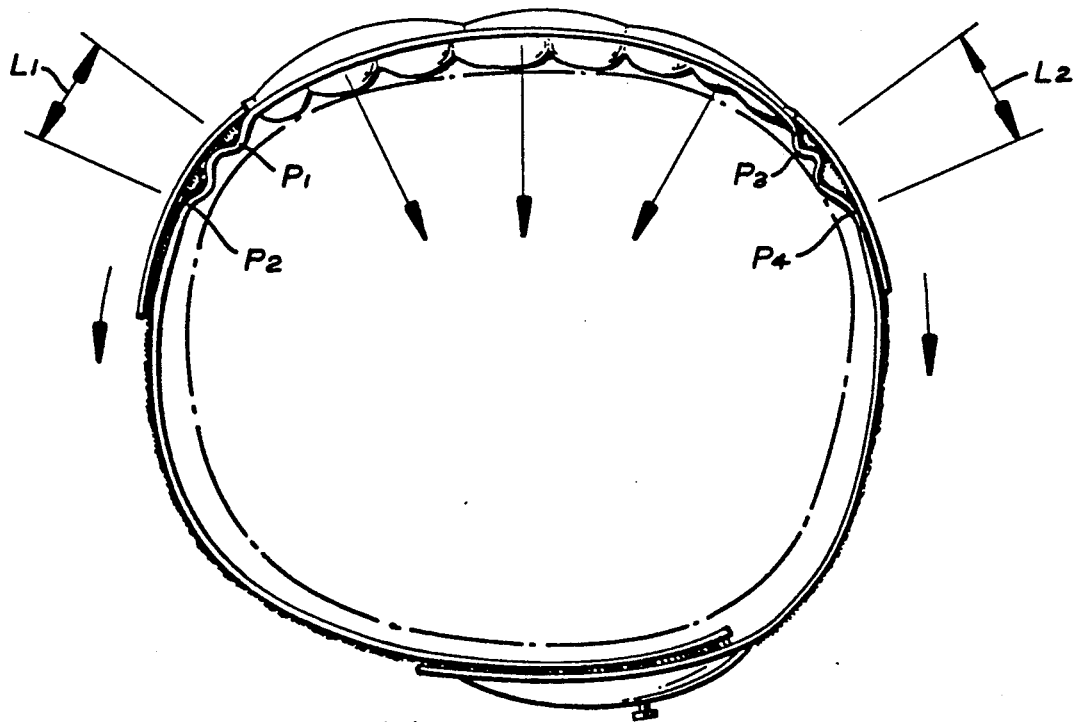

As shown in FIGS. 14(a) and 14(b), when the strap members (strap members 50 and 54 shown) are pulled laterally and engaged at new positions along the loop fabric surfaces on opposite sides of the bladder cavity, the distances (L1) and (L2) between points (P1) and (P2) and (P3) and (P4), respectively, on opposite sides of the belt structure reduced. The net effect is that the overall circumference of the belt structure 14 is reduced which forces the air bladder into the lower back.

In each air bladder positioning embodiment described above, the strap members 50, 54, 58, 63, 67, 71, and 81 are made of elastic material which is sufficiently rigid to exert the horizontal and diagonal forces shown in FIGS. 10-14. In addition, the elastic material must be sufficiently rigid to reduce the length of the sides of the belt structure 14 as shown in FIGS. 14(a) and 14(b). In the preferred embodiment they are made of elastic material made of 88% polyester and 12% rubber with 90% (+/− 10%) elongation. Horizontal straps members 50 and 54 measure approximately 8-¼ inches (L)×2 inches (W). Diagonal strap members 58, 63, 67, and 71 measure approximately 9 inches (L)×2 inches (W). Free floating horizontal strap member 81 measures approximately 17 inches (L) and 2 inches (W).

In operation, the user wraps the belt structure 14 around the waist so that the air bladder 40 is placed adjacent to the lower back. The second end 17 of the belt structure 14 is then pulled over the abdomen. The first end 16 is then pulled over the second end 17 and over the fourth section 37 until a desirable length of belt structure 14 is selected. In most situations, the user adjusts the belt structure 14 so that it fits loosely around the waist. Typically, a space of approximately two inches is created between the inside surface 18 of the belt structure 14 and the user's abdomen. Once the belt structure 14 has been initially wrapped around the waist, pad 37 located on the inside surface of the belt structure 14 is pressed firmly into the loop fabric material located on the fourth section 37 of the belt structure 14 to adjustably hold the belt structure 14 around the waist.

After the pad 37 has engaged the outside surface, the user then closes the two-way valve 78. The user then manually squeezes the hand pump 77 to partially inflate the air bladder 40. The user continues to inflate the air bladder 40 until slight to moderate pressure is exerted by the air bladder 40 on the lower back. Next, the user can either relocate the pad 37 on the outside surface to adjust the length of the belt structure 14 or relocate the extending ends of the strap members to change the force exerted by the air bladder 40 on the lower back. The amount of force selected by the user depends upon the amount of support required and comfort. The direction of force will also depend upon which adjustable air bladder positioning means embodiment is used with the belt structure 14. In some instances, air may be added or released from the air bladder 40 to obtain optimal support or comfort. As the user moves or changes activities, the belt length, the amount of air in the air bladder, and the straps can be adjusted again for optimal support and comfort.

Using the back support device described herein, a novel method of providing back support to the lower back is provided. The method comprises the following steps:

a. selecting an adjustable back support device around the waist, the back support 10 comprising a belt structure 14 capable of being placed around the waist, the belt structure 14 having a first end 16, a second end 17, the belt structure 14 having an adjustable belt holding means attached thereto capable of adjustably holding the belt structure 14 around the waist, the belt support device 10 having an inflatable air bladder 40 disposed therein so that when the back support device 10 is worn around the waist, the air bladder 40 is positioned adjacent to the lower back, the belt structure 14 having an adjustable air bladder positioning means disposed between the air bladder and the belt structure capable of controlling the forces exerted by the air bladder on the lower back when the back support device is used, the belt structure having a hand pump 77 disposed therein near the first end 16 and connected to the air bladder 40, the hand pump 77 having a two-way valve 78 capable of controlling the amount of air in the air bladder 40;

b. attaching the back support device 10 by wrapping the belt structure around the waist so that the air bladder is disposed adjacent to the lower back, the engaging the adjustable belt holding means to secure the belt structure device 10 round the waist;

(c) closing the two-way valve 78;

(d) pumping the hand pump 77 to inflate the air bladder 40;

(e) adjusting the adjustable air bladder positioning means to curve the air bladder 40 around the waist and to force the air bladder 40 into the lower back;

(f) adjusting the adjustable air bladder positioning means to provide optimal support to the lower back and comfort, and;

(g) removing the belt structure from the waist by disengaging the adjustable belt holding means.

Between steps (e) and (f) above the following steps could be used to provide optimal support to the lower back. The additional steps include: step (h) adjusting the adjustable belt holding means as needed to provide optimal support to the lower back and comfort; and step (i) adjusting the amount of air in the air bladder 40 as needed to provide optimal support to the lower back and comfort;

In compliance with the statute, the invention has been described in language more or less specific as to structural features. It is understood, however, that the invention is not limited to the specific features shown since the means and construction herein disclosed comprise a preferred form of putting the invention into practice. The invention is, therefore, claimed in any of its forms or modifications within the legitimate and valid scope of the appended claims, appropriately interpreted in accordance with the doctrine of equivalents.

We claim:

1. A back support device, comprising:

a. a belt structure capable of being placed around the waist area of a user, said belt structure having a first end, a second end, an outside surface, an inside surface and an longitudinal axis, said belt structure being constructed to be not stretchable along said longitudinal axis, said outside surface being made of loop fabric material;

b. an adjustable belt holding means attached to said belt structure capable of adjustably holding said belt structure around said waist of said user during use, said adjustable belt holding means comprises a pad hook fabric material attached to said inside surface of said belt structure near said first end capable of engaging said outside surface to adjustably hold said belt structure around said waist;

c. an inflatable air bladder disposed inside said belt structure, said belt structure being disposed therein so that said air bladder is positioned adjacent to said user's lower back when said belt structure is placed around said waist, said air bladder having an upper section, a middle section, a lower section, and a vertical mid-line axis;

d. an adjustable air bladder positioning means disposed between said belt structure and said air bladder, said adjustable air bladder positioning means being capable of forcibly curving said air bladder around said waist and adjusting the force exerted by said air bladder on said lower back when said back support device is placed around said waist, said adjustable air bladder positioning means includes two elastic, horizontal strap members, each said horizontal strap member having a first end and a second ned, each said first end being attached to said air bladder along said vertical mid-line axis, each said horizontal strap member being extended in opposite directions thereof laterally across said middle section of said air bladder, said adjustable air bladder positioning means also including a hook fabric pad attached to each said horizontal strap member near said second end, said hook fabric pad being capable of selectively engaging said loop fabric material located on said outside surface of said belt structure, and;

e. an air inflation means attached inside said belt structure and connected to said air bladder, said air inflation means comprising a hand pump and a two-way value, said two-way valve being capable of controlling the amount of air in said air bladder.

2. A back support device as recited in claim 1, wherein said adjustable air bladder positioning means further comprises, two downward, diagonal strap members, each said downward, diagonal strap member having a first end and a second end, each said first end being attached to said air bladder substantially at said vertical mid-line axis and above the attachment point of said lower horizontal member; said second end of each said downward, diagonal strap member being attached to said second end of said horizontal strap member located on same side of said air bladder.

3. A back support device, comprising:
a. a belt structure capable of being placed around the waist area of an user, said belt structure having a first end, a second end, an outside surface, an inside surface and a longitudinal axis, said belt structure being constructed to be not stretchable along said longitudinal axis, said outside surface being made of loop fabric material;
b. an adjustable belt holding means attached to said belt structure capable of adjustably holding said belt structure around said waist of said user during use, said adjustable belt holding means comprises a pad hook fabric material attached to said inside surface of said belt structure near said first end capable of engaging said outside surface to adjustable hold said belt structure around said waist;
c. an inflatable air bladder disposed inside said belt structure, said belt structure being disposed therein so that said air bladder is positioned adjacent to said user's lower back when said belt structure is placed around said waist, said air bladder having an upper section, a middle section, a lower section, and a vertical mid-line axis;
d. an adjustable air bladder positioning means disposed between said belt structure and said air bladder, said adjustable air bladder positioning means being capable of forcibly curving said air bladder around said waist and adjusting the force exerted by said air bladder on said lower back when said back support device is placed around said waist, said adjustable air bladder positioning means comprising two downward, diagonal strap members, each said downward, diagonal strap member having a first end and a second end, each said first end being attached to said air bladder along said vertical mid-line axis, each said downward, diagonal strap member being disposed downward and diagonally across said upper section of said air bladder; said adjustable air bladder also comprising two upward, diagonal strap members, each said upward, diagonal strap member having a first end and a second end, each said first end being attached to said air bladder along said vertical mid-line axis on said lower section thereof, said second end of each upward, diagonal strap member being attached to said second end of said downward, diagonal strap member, and a hook fabric pad attached to said second end of said inner most said downward or upper diagonal strap member, said hook fabric pad being capable of selectively engaging said loop fabric material located on said outside surface of said belt structure, and;
e. an air inflation means attached inside said belt structure and connected to said air bladder, said air inflation means comprising a hand pump and a two-way value, said two-way valve being capable of controlling the amount of air in said air bladder.

4. A back support device as recited in claim 3, wherein said adjustable air bladder positioning means further comprising, an elastic, free floating horizontal strap member attached between said second ends of adjoining said downward and upward diagonal strap members and positioned across said middle section of said air bladder.

5. A back support device, comprising:
a. a belt structure capable of being placed around the waist area of an user, said belt structure having a first end, a second end, an outside surface made of loop fabric material, an inside surface, a tongue cavity having an outside surface formed near said first end, and a bladder cavity formed approximately centrally therein;
b. a pad of hook fabric material attached to said inside surface of said belt structure near said first end capable of engaging said outside surface of said belt structure to adjustably hold said belt structure around said waist area of said user of said device;
c. an inflatable air bladder disposed inside bladder cavity, said air bladder having an upper section, a middle section, a lower section, and a vertical midline axis;
d. an adjustable air bladder positioning means disposed between said belt structure and said air bladder, said adjustable air bladder positioning means being capable of forcibly curving said air bladder around said waist area and adjusting the force exerted by said air bladder on said lower back when said back support device is placed around said waist area, said adjustable air bladder positioning means including two elastic, horizontal strap members, each said horizontal strap member having a first end and a second end, each said first end being attached to said air bladder along said vertical mid-line axis, each said horizontal strap member being extended in opposite directions thereof laterally across said middle section of said air bladder, said adjustable air bladder positioning means also including a hook fabric pad attached to each said horizontal strap member near said second end, said hook fabric pad being capable of selectively engaging said loop fabric material located on said outside surface of said belt structure;
e. a hand pump disposed inside said tongue cavity of said belt structure, said hand pump being connected to said air bladder to inflate said air bladder, and;
f. a two-way valve attached to said hand pump enabling said user to control the amount of air in said air bladder.

6. A back support device as recited in claim 5, wherein said adjustable air bladder positioning means further comprises, two downward, diagonal strap members, each said downward, diagonal strap member having a first end and a second end, each said first end being attached to said air bladder substantially at said vertical mid-line axis and above the attachment point of said lower horizontal member; said second end of each said downward, diagonal strap member being attached to said second end of said horizontal strap member located on said side of said air bladder.

7. A back support device, comprising:
a. belt structure capable of being placed around the waist area of a user, said belt structure having a first end, a second end, an outside surface made of loop fabric material, an inside surface, and a tongue cavity having an outer surface formed near said first end, and a bladder cavity formed approximately centrally therein;

b. a pad of hook fabric material attached to said inside surface of said belt structure near said first end capable of engaging said outside surface to adjustably hold said belt structure around said waist of a user of said device;

c. an inflatable air bladder disposed inside bladder cavity, said air bladder having an upper section, a middle section, a lower section, and a vertical mid-line axis;

d. an adjustable air bladder positioning means disposed between said belt structure and said air bladder, said adjustable air bladder positioning means being capable of forcibly curving said air bladder around said waist and adjusting the force exerted by said air bladder on said lower back when said back support device is placed around said waist, said adjustable air bladder positioning means includes two downward, diagonal strap members, each said downward, diagonal strap member having a first end and second end, each said first end being attached to said air bladder along said vertical mid-line axis, each said downward, diagonal strap member being disposed downward and diagonally across said upper section of said air bladder, said adjustable air bladder positioning means also including two upward, diagonal strap members, each said upward, diagonal strap member having a first end and a second end, each said first end being attached to said air bladder along said vertical mid-line axis on said lower section thereof, said second end of each upward, diagonal strap member being attached to said second end of said downward, diagonal strap member, and; a hook fabric pad attached to said second end of said inner most said downward or upper diagonal strap member, said hook fabric pad being capable of selectively engaging said loop fabric material located on said outside surface of said belt structure;

e. a hand pump disposed inside said tongue cavity of said belt structure, said hand pump being connected to said air bladder to inflate said air bladder, and;

f. a two-way valve attached to said hand pump enabling said user to control the amount of air in said air bladder.

8. A back support device as recited in claim 7, wherein said adjustable air bladder positioning means further comprising, an elastic, free floating horizontal strap member attached between said second ends of adjoining said downward and upward diagonal strap members and across said middle section of said air bladder.

9. A method of providing support to the lower back, comprising the following steps:

a. selecting an adjustable back support device around the waist, said back support comprising a belt structure capable of being placed around said waist, said belt structure having a first end, a second end, said belt structure having an adjustable belt holding means attached thereto capable of adjustably holding said belt structure around said waist, said belt support having an inflatable air bladder disposed therein so that when said back support is worn around said waist, said air bladder is positioned adjacent to said lower back, said belt structure further including an adjustable air bladder positioning means disposed between said air bladder and said belt structure capable of controlling the forces exerted by said air bladder on said lower back, when said back support device is used, said adjustable air bladder positioning means includes two elastic, horizontal strap members, each said horizontal strap member having a first end and a second end, each said first end being attached to said air bladder along said vertical mid-line axis, each said horizontal strap member being extended in opposite directions thereof laterally across said middle section of said air bladder, said adjustable air bladder positioning means also including a hook fabric pad attached to each said horizontal strap member near said second end, said hook fabric pad being capable of selectivity engaging said loop fabric material located on said outside surface of said belt structure, said belt structure having a hand pump disposed therein near said first end and connected to said air bladder, said hand pump having a two-way valve capable of controlling the amount of air in said air bladder;

b. attaching said back support device by wrapping said belt structure around said waist so that said air bladder is disposed adjacent to said lower back, said engaging said adjustable belt holding means to secure said belt structure around said waist;

(c) closing said two-way valve;

(d) pumping said hand pump to inflate said air bladder;

(e) adjusting said horizontal strap members on said outside surface of said belt structure so that said air bladder curves around said waist to force said air bladder into said lower back;

(f) adjusting said strap members to provide optimal support to said lower back and comfort, and;

(g) removing said belt structure from said waist by disengaging said adjustable belt holding means.

10. The method disclosed in claim 9, further including step (h) between steps (f) and (g), step (h) comprising:

adjusting said horizontal strap members on said outside surface of said belt structure as needed to provide optimal support to said lower back and comfort;

11. The method disclosed in claim 9, further including step (i) between steps (f) and (g), step (i) comprising:

adjusting the amount of air in said air bladder as needed to provide optimal support to said lower back and comfort;

* * * * *